United States Patent [19]

Gruner et al.

[11] Patent Number: 4,588,698
[45] Date of Patent: May 13, 1986

[54] ENCAPSULATED SCINTILLATORS FOR MEASURING THE CONCENTRATION OF TRITIATED SOLUTES

[75] Inventors: Sol M. Gruner, Lawrenceville; Gregory Kirk, Princeton, both of N.J.

[73] Assignee: University Patents, Inc., Westport, Conn.

[21] Appl. No.: 435,528

[22] Filed: Oct. 19, 1982

[51] Int. Cl.$^4$ ................ G01N 33/54; G01N 33/56
[52] U.S. Cl. ........................... 436/535; 252/301.17; 422/71; 436/57; 436/804; 436/805; 436/808; 436/829
[58] Field of Search ............ 436/535, 829, 57, 804, 436/805, 808; 422/71; 252/301.17

[56] References Cited

U.S. PATENT DOCUMENTS

| | | | |
|---|---|---|---|
| 3,793,445 | 2/1974 | Updike | 436/535 |
| 4,000,252 | 12/1976 | Kosak | 436/535 X |
| 4,062,799 | 12/1977 | Matsukawa | 436/829 X |
| 4,066,568 | 1/1978 | Nakazawa | 436/829 X |
| 4,127,499 | 11/1978 | Chen | 252/301.17 |
| 4,193,983 | 3/1980 | Ullman | 436/535 X |
| 4,311,690 | 1/1982 | Buehler | 436/829 X |
| 4,396,528 | 8/1983 | Abbott | 252/301.17 |

OTHER PUBLICATIONS

Chemical Abstracts, 86:80633x (1977).
Chemical Abstracts, 97:20223f (1982).

*Primary Examiner*—Sidney Marantz
*Attorney, Agent, or Firm*—George M. Yahwak

[57] ABSTRACT

Microencapsulation of solid phase scintillators in gels selectively permeable to diffusible radioactive label. These encapsulated scintillators are used to monitor the concentration of radioactive-tagged subtances in fluid systems.

14 Claims, 1 Drawing Figure

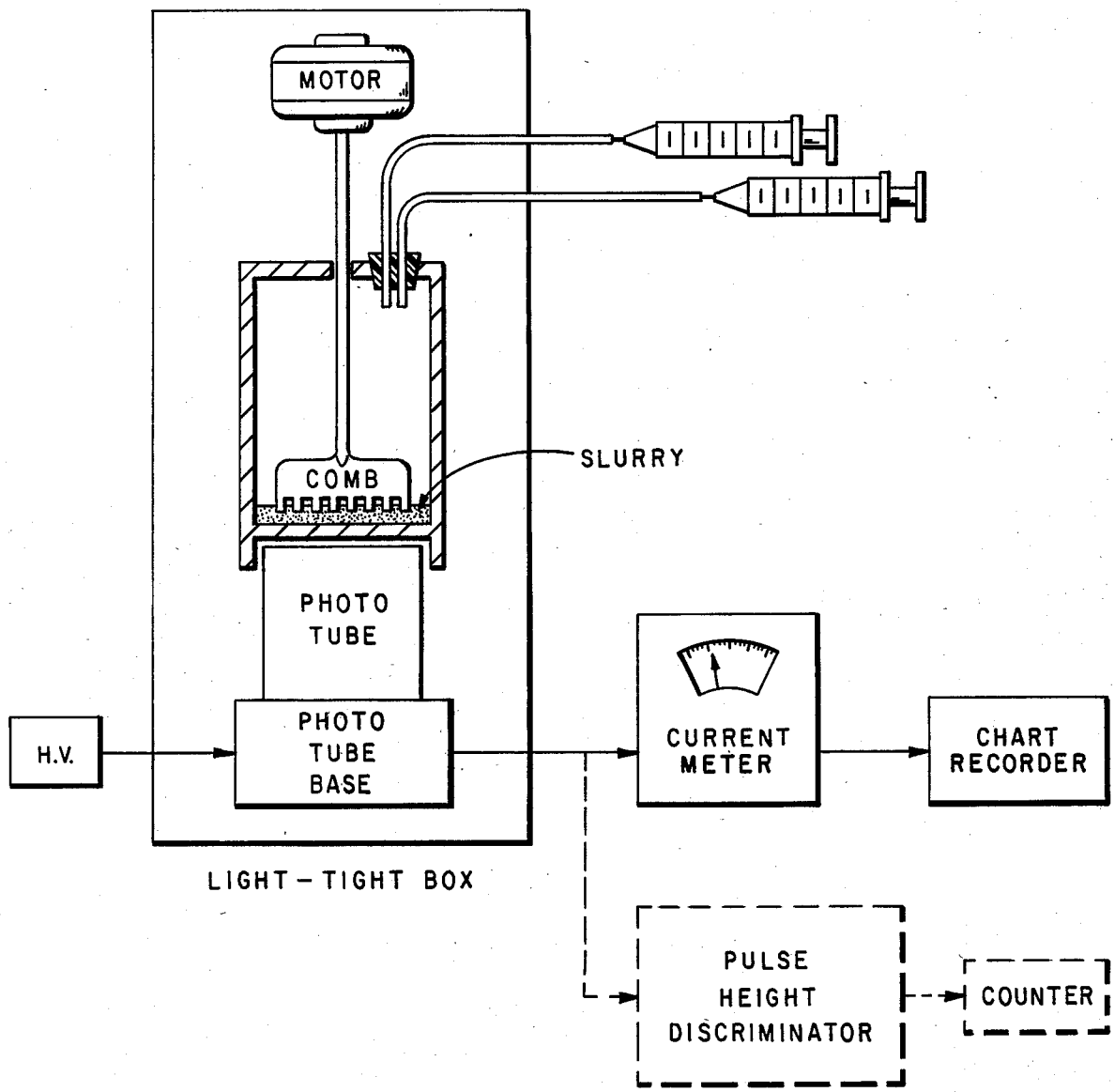

ENCAPSULATED SCINTILLATORS FOR MEASURING THE CONCENTRATION OF TRITIATED SOLUTES

BACKGROUND OF THE INVENTION

The present invention relates to a new and novel microencapsulation of solid phase scintillators in gels that are permeable to selected diffusible labels carrying radioactive sources capable of activating the encapsulated scintillator. These microencapsulated scintillators have been used to develop a method for dynamically monitoring the free concentration of diffusible, radioactive-tagged substances in fluid systems.

In biological systems, it is frequently important to quantify uptake, binding, or release of soluble substances by colloidal or macroscopic phases such as cells, sub-cellular particles, or macromolecules. Examples include cellular uptakes of various drugs, the release of cellular catabolites into the blood stream, blood serum levels of various drugs, enzymes, and hormones, and the presence or absence of specific immunoglobulins in the serum of a patient.

Generally, uptake or release is measured either directly by assaying the macroscopic phase after separation from its normal bathing medium, or indirectly by determining the free concentration of the solute. Although a wide variety of analytical techniques (see, for example, S. Ramos, S. Schuldiner, and H. R. Kaback, *Methods in Enzymology*, Volume IV, part F, pages 680–688; Academic Press, New York 1979) are currently used to obtain these measurements, no single procedure is applicable in every instance. Most procedures are either relatively insensitive, exhibit poort time resolution, or are applicable to a relatively limited group of solutes.

SUMMARY OF THE INVENTION

The present invention relies upon the fact that certain radiolabels, most notably tritium, release beta radiation which has a very limited range. For example, the tritium beta emission has a range of only about 7 micrometers in water. Consequently, microscopic particles of a scintillating material need only be microencapsulated with a thin (more than 7 $\mu$m) coating to exclude all exciting radiation from tritium bound to material which cannot penetrate the encapsulation, i.e., a scintillator may be totally shielded from a tritiated source that is not freely diffusible. If the coating, is however, permeable to small tritiated molecules but not to larger objects, i.e., the macrophase, then the scintillator will be excited only by the small molecules which are free in the solution and are able to pass through the encapsulation. The advantage of using microscopic scintillator particles is that the scintillator particles and macroscopic phase may be very intimately mixed in the solution. Furthermore, the surface area to volume ratio of the scintillator particles can be made very large if the scintillator is finely divided; this improves the scintillator detection efficiency to low energy beta radiation.

The tritium isotope has the desirable characteristics of decaying via the emission of a low energy electron ($E_{ma} = 18.6$ keV; mean weighted energy $= 6.3$ keV) and of being incorporated into many organic compounds. Other Beta emitters may also be used such as carbon-14, sulphur-35, and phosphorous-32. However, the thickness of the gel encapsulation must be increased with increased Beta energy, and therefore low energy Beta emitters, such as tritium, are preferred. As the emitted Beta electron from tritium is responsible for the resultant photon emission of the scintillator, the range, (that is the distance required between the tritium atoms and the target surface, which reduces the energy deposited beyond the surface to some nominal fraction of the energy emitted) appropriate to the tritium Beta-ray spectrum is approximately 1 micrometer in materials with the density of water. Thus, an effective aqueous shield to Beta radiation need only be a few micrometers thick.

In order to provide that a tritiated molecule sequestered by the macrophase—e.g. colloidal phase, cells, vesicles, or macromolecules—is unable to excite a scintillator bead, it is desirable that the scintillator beads be segregated from the macrophase being monitored.

We have discovered that segregation of the macrophase from the scintillator can be accomplished by providing a selective permeable coating about the scintillator. These coatings may be composed of suitable hydrophilic materials capable of encapsulating the scintillator such as, for example, coatings of carbohydrate origin such as gelatin or agarose, or various gels such as polyacrylamide gel. Other materials may also be used to encapsulate the scintillator, for example, non-hydrophilic material, or hydrophobic materials may also be utilized depending upon the test medium. For the purpose of this discussion, all selective permeable coatings will be referred to as "gels".

Simplistically, one embodiment of our procedure allows for a finely divided scintillator to be encapsulated as microbeads in a selectively permeable gel. The selective permeability of the gel is achieved by selecting a gel pore size (in accordance, for example, with the procedure of L. Ornstein, *Annals of New York Academy of Science*, 121:321-349, the disclosure of which is hereby incorporated) large enough to allow for diffusion of the tritiated solute in solution through the pore while excluding larger molecules—including the tritiated solute when complexed with another macrophase—from exciting the encapsulated scintillator. As a result, the scintillation light output continuously monitors the free concentration of the tritiated species with no contribution from solute that is not freely diffusible.

The microencapsulated beads of the present invention may be used in the determination of substances in many fluids such as body or aqueous fluids. As an example, consider a determination based upon general radioimmunoassay techniques known in the art. For example, if a test was required to determine the concentration of a given drug in blood serum, antibodies, including monoclonal antibodies or antibodies prepared by other means, to the drug would be prepared, isolated and purified. This antibody would then be mixed with the blood serum, and encapsulated scintillators, made according to the present invention would be added. The pore size of the gel encapsulation would be chosen small enough to exclude antibody drug molecule complexes but not antibody with drug molecules attached. If the blood serum contained the drug, the antibody would bind with the drug to form an antigen-antibody complex. When tritiated-labelled drug is then added, the drug would not be bound to the antibody, and would be free to diffuse through the pores of the gel coating to excite the scintillator. If the blood serum does not contain any of the drug, the antibody would bind to a subsequent addition of tritiated-labelled drug, and the scintillator would not be excited. Furthermore, by serial dilutions of a known antigen standard amount, a standardized curve may be obtained from which the titer of bound antibody in a sample can be calculated.

Alternately, the blood serum or other body fluid may be pretreated to purify any antigen present by removing possible interferring substances which might cause anomalies with the test. For example, in the data presented in Table 1, the test media is an aqueous solution, and to achieve similar sensitivities in samples of blood serum, interfering substances such as albumin, immunoglobulins, and other protein fractions should be removed. This would be accomplished by conventional separation techniques, such as precipitation, or chromatrographic techniques. Other body fluids, for example saliva or urine, might undergo similar separation, i.e. purification, pretreatment. If, on the other hand, the gel was chosen to be compatible with the test media, no pretreatment would be necessary.

Various scintillation means have previously been used to determine the presence of various immunospecific substances.

U.S. Pat. No. 4,000,252 for an "Immunoscintillation Cell" discloses an immunoscintillation composition used in a solid phase radioimmunoassay. In this immunoassay, a mixture of labeled and unlabeled antigens is introduced into a cell containing solid, insolubilized or coated scintillators and solid or insolubilized antibodies which selectively retain a portion of the labeled and unlabeled antigens. In one embodiment of the invention, scintillators and antibodies are chemically bound to an insoluble substrate; in another embodiment, the phosphor and the antibodies are maintained separately by means of a protective material. In both embodiments, the radioactive energy released by the labeled antigen excites the scintillators releasing burst of photons which are measured by appropriate means. Studies have shown that the counted or measured photons are proportional to the concentration of labeled antigens bound to the antibodies.

As shown in FIG. 2 of the Immunoscintillation Cell patent, the scintillators are embedded within the sides of a tube, or, in FIG. 4, within plastic balls. This "protection" of the scintillators is not for the purpose of maintaining any particular separation between the scintillator and the radioactive label located elsewhere in the system, but rather for the purpose of preventing the scintillators from contaminating each other and for preventing the scintillators from being solubilized from the carrier solvent. It differs, most importantly, from the present invention by not utilizing a selectively permeable scintillator coating.

Similarly, U.S. Pat. No. 4,271,139 presents a "Scintillation Proximity Assay" as an improvement over conventional immunoassay latex fixation tests. Briefly, the purpose of the technique disclosed in this patent is to measure the degree of linking or proximity of one type of latex particle (type A) to polystyrene scintillant particles (type B). This invention takes advantage of the limited range of the particular radiation employed (about 1 $\mu$m) in aqueous media emitted from a tritiated type A particle. When type A and type B particles are "tagged" with antigen and antibody, respectively, the amount of particle aggregation resulting from the concentration of antigen (or antibody) present can be determined using liquid scintillation counting equipment; if the type A and B particles are separated, i.e., no immunomediated aggregation, the radiation from the type A particle is attenuated in liquid and never reaches the scintillator type B particles to release photons.

DESCRIPTION OF THE DRAWING

In order to more fully understand the present invention, references will be made to the drawings in which:

FIG. 1 is a schematic of a simple embodiment showing the apparatus used to detect the light output of the scintillator bead-macrophase slurry.

The radioactively-induced scintillation may be detected with the apparatus similar to that illustrated in FIG. 1. Several milliliters of a mixture of the macrophase to be monitored, a tritiated substrate, and the gel-bead slurry prepared in accordance with Example 2 were contained (to a depth of 1-2 mm) in a polished lucite cylinder, which was coupled with optical grease to the face plate of an RCA 8850 photomultiplier tube. The photomultiplier tube was operated at $-2000$ volts (sufficient to give a photoelectron gain of about $8 \times 10^6$), and the output current from the tube was read on an ampmeter (in the case of the system actually used, output was read directly on a Keithley 610C electrometer). Typical dark currents, that is background "noise", for the photomultiplier, after dark adaptation, were about $10^{-9}$ Amperes. The slurry was continuously stirred by a motor driven comb cut from a thin sheet of Teflon, and fitted on a long shaft sufficient to allow the motor to be located at a distance sufficient so the motor fields did not affect the photomultiplier. The entire photomultiplier-cylinder-motor apparatus was enclosed in a light-tight box with openings limited for tubing allowing the addition of substrate by injection.

An alternative, and more sensitive, means for recording the output current from the photomultiplier tube, such as the pulse height discriminator-counter system is indicated by phantom lines in FIG. 1. By such a means it would be possible to directly omit the background noise, or dark current, being emitted from the tube.

Other modifications could also be made, and are well within the skills of the manufacturer of such instrumentation. The mixing, for example, could be accomplished by means other than the motor-shaft-comb combination, that is equal mixing may be accomplished by using magnetic stirrers or other devices. Also, the cylinder does not necessarily need to be of lucite, for example, equally useful cylinders may be composed of other non-scintillator materials such as silica.

The scintillator and slurry preparations used to demonstrate the feasibility of the method were made as described in the following examples, which are given for the purpose of more clearly illustrating the invention.

EXAMPLE 1

SCINTILLATOR PREPARATION

Two grams of Polyvinyltouluene based NE 102 plastic scintillator microspheres of 1-10 um diameter (Nuclear Enterprises, Inc., San Carlos, Calif.) were suspended in 20 ml of 3% Triton X-100 surfactant by vortexing and gentle sonication. The detergent was required because the beads are difficult to wet. The detergent was then removed by five or six water washes. For each wash, the beads were sedimented by centrifugation at $6000 \times g$ for 10 minutes. After each sedimentation, the supernatant was discarded and the beads re-suspended in 30 ml of distilled water. After the final wash, the re-suspended beads were allowed to settle overnight, and the supernatant was carefully removed. The resultant slurry was roughly 10% beads by volume.

EXAMPLE 2

ENCAPSULATION

The following quantities were used, for each ml of settled bead slurry, to produce a polyacrylamide gel: 300 mg acrylamide and 1.5 mg N,N'-methylene-bisacrylamide were dissolved in the slurry. Polymerization was catalyzed by the addition of 10 ul of 10% (w/v) ammonium persulfate solution and 2 μl of N,N,N',N-tetramethyl-ethylenediamine (TEMED). The polymerized gel was cut into pieces, suspended in distilled water, and then sheared in a blender for several minutes to a uniform consistency of fine particles. Microscopic examination of the product revealed irregularly shaped bits of gel (mean size 0.1 mm) encasing clumps of scintillator. the scintillator to gel volume ratio was about 10%. The gel particles were allowed to settle after the supernatant was discarded, and the final slurry was refrigerated until used.

Although the gel used to provide the microencapsulation of the scintillator was polyacrylamide, other materials may also be used such as gelatin, agarose, etc. The requirements for the coating being the ability to encapsulate with well defined pore sizes and therefore being permeable to the label but not to the macrophase. The reason polyacrylamide was chosen, in fact, was becuase it has been extensively characterized how to obtain various pore sizes with this material.

Although the scintillators following this treatment may appear as single, double, or multiple hydrophobic or hydrophilic scintillator beads within an encapsulating material, the ideal microencapsulated scintillator is a single particle surrounded by a layer of the encapsulating material. While single, double, or multiple encapsulations of scintillator may be used in the method of the present invention, provided the pores of such are large enough to allow for the diffusion of the labelled, unbound component, the single encapsulated scintillator is favored because of economic, both cost and reactivity, factors. Further, single encapsulated scintillator has an advantageous time response by reducing the thickness of gel through which the labelled compound must diffuse. Also, in order to achieve compatability with the unknown component, each scintillator may be coated with more than one layer of material, for example by coating the scintillator using glycophase coating technology common in chromatography preparation.

The data obtainable by our method of preparing a radioimmunoassay using microencapsulated scintillator according to our invention, and made in accordance with Examples 1 and 2, are shown in Table 1 in which each indicated run is the mean value of two separate runs. In each instance, the tritiated compound used as the labeled compound is tritiated chlorpromazine, and the antibody is chlorpromazine antibody prepared in accordance with accepted practice.

The test media in this instance is water, not body fluid, the substitution of which would cause the sensitivity (CPM) of the test to be lower, but still acceptable, because of inteferring substances normally contained in various body fluids; this decrease in sensitivity would be overcome by an increase in the number of encapsulated scintillators.

TABLE 1

| Run | Bead | [³H] | H₂O | [AB] | CPM |
| --- | --- | --- | --- | --- | --- |
| 1 | — | 100λ | 0.4 ml | — | 14 |
| 2 | 50λ | — | 0.45 ml | — | 17 |
| 3 | 50λ | 100λ | 0.35 ml | — | 251,296 |
| 4 | — | 100λ | 0.4 ml | — | 15 |
| 5 | 50λ | — | 0.45 ml | — | 18 |
| 6 | 50λ | 100λ | 0.35 ml | — | 234,499 |
| 7 | 100λ | 100λ | 0.25 ml | 100 | 11,947 |

[³H] Refers to the concentration of tritium-labelled antigen; 100λ being the equivalent of approximately 3 micrograms of antigen.
[AB] Refers to the concentration of affinity purified antibody to chlorpramazine; 100λ being equivalent to approximately 100 micrograms of antibody.

Bead refers to the concentration of gel encapsulated beads made in accordance with Example 2; 50λ being equivalent to approximately 10 milligrams of beads.

The data contained in Table 1 clearly establishes that when either the label (runs 1 and 4) or the microencapsulated scintillator (runs 2 and 5) is present alone in the system, only background counts (dark current) are registered. On the other hand, when both components are present together (runs 3 and 6) the labelled compound is able to diffuse through the coating about the scintillator, and the resulting photo emission is increased to a much greater number. When, in addition to the microencapsulated scintillator and the tritiated label, chlorpromazine antibody is also added to the system, (run 7) a substantial decrease in counts is observed. This clearly indicates that the immune complex formed between the labelled substrate and the antibody does not penetrate the scintillator coating.

The feasibility of using a immunoassay system for unknowns based upon our invention is clearly established. Unknown titers could be detected by establishing a standard curve in the usual manner with varying concentrations of the target substance determining the unknown titer from the curve relative to the counts observed.

As discussed previously, our invention may be used to determine the levels of various drugs, hormones, and enzymes in blood serum or other body fluids such as saliva or urine. The encapsulated scintillator beads may also be used to conduct rate uptake studies such as described in our publication: "A Method For Rapid, Continuous Monitoring Of Solute Uptake and Binding", *Biochemistry* 1982, 21,3239, the disclosure of which is hereby incorporated in toto. The encapsulated scintillator beads may also be used in receptor binder assays, for example, estrogens, acetylcholine, opiate peptides, and others.

From the foregoing description, one skilled in the art can easily ascertain the essential characteristics of this invention and without departing from the spirit and scope thereof can make various changes and/or modifications to the invention for adapting it to various usages and conditions. Thus, while we have illustrated and described the preferred embodiment of our invention, it is to be understood that this is capable of variation and modification, and we therefore do not wish to be limited to the precise terms set forth, but desire to avail ourselves of such changes and alterations which fall within the purview of the following claims:

We claim:

1. A composite material comprising a microencapsulated central solid scintillator core capable of releasing photons when exposed to a source of radiation, and a selective permeable coating about said core, said coating having a width at least as wide as the range of radioactivity of said radiation.

2. The composite according to claim 1 wherein the coating is permeable to selected diffusible labels carrying radiation sources capable of activating the scintillator core to release photons.

3. The composite according to claim 1 wherein the radiation source is a Beta ray source.

4. The composite according to claim 3 wherein the coating is selected from the group consisting of hydrophilic, non-hydrophilic, and hydrophobic materials.

5. The composite according to claim 4 wherein the Beta ray source is tritium, and wherein the coating about said scintillator core is at least 1 micrometer in width.

6. The composite according to claim 4 wherein the hydrophilic materials are of carbohydrate origin.

7. A kit for use in the radioimmunoassay of a fluid test medium which comprises:
 (a) a quantity of scintillator material encapsulated within an encapsulating material permeable to selected diffusible labels carrying radioactive sources capable of activating the scintillator material and having a width about said material at least as wide as the range of radiation from said source;
 (b) a quantity of a beta-labelled substance capable of eliciting immune response in a biological system and capable of passing through pores of the selectively permeable coating material about said scintillator material and;
 (c) a quantity of an antibody directed towards said beta-labelled substance, wherein an immune complex between the beta labelled substance and the antibody is of sufficient size to be excluded from passing through the pores of the encapsulating material.

8. The kit according to claim 7 wherein the beta-labelled substance is tritium-labelled substance, and the width of the encapsulating material is at least 1 micrometer.

9. The kit according to claim 7 wherein the beta labelled substance is an antigen.

10. A radioimmunoassay technique for the determination of a substance in a fluid test medium which comprises:
 (1) Providing a quantity of antibody directed towards the substance to be determined to a test fluid;
 (2) providing a quantity of a beta labelled substance to said test fluid; and
 (3) providing a quantity of composite material comprising a microencapsulated central solid scintillator core capable of releasing photons when exposed to a source of radiation, and a selective permeable coating about said core, said coating having a width at least as wide as the range of radioactivity of said radiation and further having a pore size small enough to exclude antibody substance complex molecules but not antibody molecules to said incubating mixture; and
 (4) determining the amount of photons released by the scintillator core in said composite material.

11. The radioimmunoassay technique according to claim 10 wherein the test medium is a body fluid, and the substance is an antigen.

12. A process for determining in a protein-containing sample the presence of an unbound substance capable of reversibly binding to protein, said process comprising the steps of:
 (a) incubating the sample with an antibody capable of forming an antibody substance complex with said antibody.
 (b) adding a composite material comprising a microencapsulated central solid scintillator core capable of releasing photons when exposed to a source of radiation, and a selective permeable coating about said core, said coating having a width at least as wide as the range of radioactivity of said radiation and further having a pore size small enough to exclude antibody substance complex molecules but not antibody molecules to said incubating mixture;
 (c) adding a known amount of unbound radioactive-labelled substance to the sample-antibody composite mixture; and
 (d) quantitating the amount of photons released by said scintillator core.

13. The process according to claim 12 wherein said substance is selected from the group consisting of pharmaceuticals, cellular catabolites, enzymes, hormones, and immunoglobulins.

14. A method of radioimmunoassay comprising introducing a sample of body fluid containing an unknown quantity of antigenic substance to a scintillation cell; adding antibody to said antigenic substance in an amount sufficient to form an antigen-antibody complex with said antigenic substance; introducing a quantity of microencapsulated scintillator materials according to claim 1; adding a quantity of radioactively labelled antigenic substance to said cell; and measuring the photons caused to be released by the labelled substance.

* * * * *